US012616925B2

(12) United States Patent
Oestberg et al.

(10) Patent No.: US 12,616,925 B2
(45) Date of Patent: May 5, 2026

(54) OIL PURIFICATION FILTER

(71) Applicant: SKF RECONDOIL AB, Östersund (SE)

(72) Inventors: Tomas Oestberg, Froson (SE); Karl Enquist, Bromma (SE); Thomas Persson, Sandviken (SE)

(73) Assignee: SKF RECONDOIL AB, Östersund (SE)

( * ) Notice: Subject to any disclaimer, the term of this patent is extended or adjusted under 35 U.S.C. 154(b) by 726 days.

(21) Appl. No.: 17/926,430

(22) PCT Filed: Jun. 2, 2021

(86) PCT No.: PCT/EP2021/064755
   § 371 (c)(1),
   (2) Date: Nov. 18, 2022

(87) PCT Pub. No.: WO2021/245121
   PCT Pub. Date: Dec. 9, 2021

(65) Prior Publication Data
   US 2023/0182050 A1     Jun. 15, 2023

(30) Foreign Application Priority Data
   Jun. 5, 2020    (DE) .......................... 102020207112.8

(51) Int. Cl.
   *B01D 39/18*     (2006.01)
   *B01D 29/11*     (2006.01)
   (Continued)

(52) U.S. Cl.
   CPC ............ *B01D 39/18* (2013.01); *B01D 29/111* (2013.01); *B01D 29/31* (2013.01); *B01D 35/30* (2013.01);
   (Continued)

(58) Field of Classification Search
   CPC .... H04N 23/62; H04N 23/631; H04N 23/633; H04N 23/667; H04N 23/67; H04N 23/73;
   (Continued)

(56) References Cited

U.S. PATENT DOCUMENTS

| 1,951,739 A | 3/1934 | Rodman et al. |
| 2,023,988 A | 12/1935 | Bissell et al. |

(Continued)

FOREIGN PATENT DOCUMENTS

| BR | 112019022347 A2 | 5/2020 |
| CA | 2747909 C | 6/2014 |

(Continued)

OTHER PUBLICATIONS

DE102012219409 Translation (Year: 2014).*

(Continued)

*Primary Examiner* — Ellen M McAvoy
*Assistant Examiner* — Chantel Graham
(74) *Attorney, Agent, or Firm* — J-TEK LAW PLLC; Jeffrey D. Tekanic; Scott T. Wakeman

(57)     ABSTRACT

An oil purification filter for purifying a contaminated oil includes a filter body having a first portion and a second portion, where at least the first portion is impregnated with a separation aid. The separation aid is substantially insoluble in the contaminated oil because of its polar properties, and the separation aid is configured to adsorb/absorb contaminating solids or dissolved impurities in the contaminated oil by chemical interactions. The filter body may comprise one or more sheets of cellulose fibers.

21 Claims, 7 Drawing Sheets

(51) Int. Cl.

| | |
|---|---|
| *B01D 29/31* | (2006.01) |
| *B01D 35/30* | (2006.01) |
| *F16N 39/06* | (2006.01) |
| *G01N 33/28* | (2006.01) |

(52) U.S. Cl.
CPC ..... *G01N 33/28* (2013.01); *B01D 2239/0407* (2013.01); *B01D 2239/0464* (2013.01); *B01D 2239/065* (2013.01); *B01D 2239/0695* (2013.01); *B01D 2239/10* (2013.01); *F16N 39/06* (2013.01)

(58) Field of Classification Search
CPC ...... H04N 23/63; H04N 5/93; B01D 17/0202; B01D 17/047; B01D 17/10; B01D 2239/0407; B01D 2239/0414; B01D 2239/0464; B01D 2239/065; B01D 2239/0695; B01D 2239/10; B01D 29/111; B01D 29/31; B01D 35/30; B01D 39/18; F16H 57/0404; F16N 39/06; G01N 33/28
See application file for complete search history.

(56) References Cited

U.S. PATENT DOCUMENTS

| | | | |
|---|---|---|---|
| 2,049,014 A | 7/1936 | Mcafee et al. | |
| 2,248,131 A | 7/1941 | Smith | |
| 2,435,707 A | 2/1948 | Bray et al. | |
| 3,265,212 A | 8/1966 | Bonsall | |
| 3,304,255 A | 2/1967 | Kihei et al. | |
| 3,930,988 A | 1/1976 | Johnson | |
| 4,028,226 A | 6/1977 | Forsberg | |
| 4,256,578 A | 3/1981 | Kozar | |
| 4,741,840 A | 5/1988 | Atherton et al. | |
| 5,137,654 A | 8/1992 | Burke | |
| 5,154,828 A | 10/1992 | Schneider et al. | |
| 5,976,357 A | 11/1999 | Strom et al. | |
| 6,013,174 A | 1/2000 | Kovacs | |
| 6,191,077 B1 | 2/2001 | Baumgartner et al. | |
| 6,555,014 B1 | 4/2003 | Bremer et al. | |
| 8,816,105 B2 | 8/2014 | Ristolainen et al. | |
| 10,493,383 B2 | 12/2019 | Teodorescu | |
| 10,995,279 B2 | 5/2021 | Sundström et al. | |
| 11,130,075 B2 | 9/2021 | Sundström et al. | |
| 11,958,004 B2 | 4/2024 | Persson et al. | |
| 12,097,453 B2 | 9/2024 | Sundström et al. | |
| 2003/0000895 A1 | 1/2003 | Hensley et al. | |
| 2006/0000787 A1 | 1/2006 | Galasso et al. | |
| 2006/0135377 A1 | 6/2006 | Li et al. | |
| 2006/0283807 A1 | 12/2006 | Owen | |
| 2007/0241030 A1 | 10/2007 | Strom | |
| 2008/0314821 A1 | 12/2008 | Ohashi et al. | |
| 2009/0078632 A1 | 3/2009 | Gallo et al. | |
| 2011/0174695 A1 | 7/2011 | Goldman | |
| 2011/0213169 A1 | 9/2011 | Ristolainen et al. | |
| 2013/0026082 A1 | 1/2013 | Al-Shafei et al. | |
| 2013/0098805 A1 | 4/2013 | Bjornson et al. | |
| 2014/0224640 A1 | 8/2014 | Fincher et al. | |
| 2014/0332473 A1 | 11/2014 | Haberman et al. | |
| 2015/0072850 A1 | 3/2015 | Derrick et al. | |
| 2015/0152340 A1 | 6/2015 | Cherney et al. | |
| 2015/0224431 A1 | 8/2015 | Wase | |
| 2015/0265955 A1 | 9/2015 | Kanchi et al. | |
| 2015/0283487 A1 | 10/2015 | Demmel et al. | |
| 2015/0322348 A1 | 11/2015 | Dasgupta | |
| 2016/0052799 A1 | 2/2016 | Grave et al. | |
| 2016/0122209 A1 | 5/2016 | Newman, Jr. | |
| 2016/0177198 A1 | 6/2016 | Mao | |
| 2016/0207791 A1 | 7/2016 | Rabe et al. | |
| 2016/0264442 A1 | 9/2016 | Knoop | |
| 2017/0029716 A1 | 2/2017 | Dasgupta | |
| 2017/0190985 A1 | 7/2017 | Matza | |
| 2019/0192996 A1 | 6/2019 | Persson | |
| 2020/0056102 A1 | 2/2020 | Sundström et al. | |
| 2020/0230520 A1 | 7/2020 | Sundström et al. | |
| 2021/0101094 A1 | 4/2021 | Sundström et al. | |
| 2022/0016554 A1 | 1/2022 | Persson et al. | |
| 2022/0096976 A1 | 3/2022 | Mineo et al. | |
| 2022/0111317 A1 | 4/2022 | Sundström et al. | |
| 2023/0143845 A1 | 5/2023 | Enquist et al. | |
| 2023/0182050 A1 | 6/2023 | Oestberg et al. | |
| 2024/0252963 A1 | 8/2024 | Persson et al. | |

FOREIGN PATENT DOCUMENTS

| | | | | |
|---|---|---|---|---|
| CN | 85100831 A | 7/1986 | | |
| CN | 1267561 A | 9/2000 | | |
| CN | 102925275 A | 2/2013 | | |
| CN | 103111089 A | 5/2013 | | |
| CN | 104662139 A | 5/2015 | | |
| CN | 104902980 A | 9/2015 | | |
| CN | 105457606 A | 4/2016 | | |
| CN | 205133522 U | 4/2016 | | |
| CN | 107158744 A | 9/2017 | | |
| CN | 110769910 A | 2/2020 | | |
| DE | 19522596 A1 | 1/1997 | | |
| DE | 102009006586 A1 | 6/2010 | | |
| DE | 102012219409 A1 * | 4/2014 | .......... | B01D 39/163 |
| EP | 0693544 A2 | 1/1996 | | |
| EP | 1561797 A1 | 8/2005 | | |
| EP | 2181744 A1 | 5/2010 | | |
| EP | 2900798 B1 | 11/2017 | | |
| ES | 2374247 A1 | 2/2012 | | |
| FI | 20105121 A | 8/2011 | | |
| GB | 500433 A | 2/1939 | | |
| GB | 547020 A | 8/1942 | | |
| GB | 758747 A | 10/1956 | | |
| GB | 1041703 A | 9/1966 | | |
| GB | 1294861 A | 11/1972 | | |
| GB | 1450673 A | 9/1976 | | |
| GB | 2107347 A | 4/1983 | | |
| GB | 2334034 A | 8/1999 | | |
| JP | S60135483 A | 7/1985 | | |
| JP | S6351903 U | 4/1988 | | |
| JP | 2001239111 A | 9/2001 | | |
| JP | 2016161464 A | 9/2016 | | |
| WO | 2005111181 A1 | 11/2005 | | |
| WO | 2017196234 A1 | 11/2017 | | |
| WO | 2018199838 A1 | 11/2018 | | |
| WO | 2018199839 A1 | 11/2018 | | |
| WO | WO-2018199837 A1 * | 11/2018 | ............ | B01D 21/30 |
| WO | 2020162815 A1 | 8/2020 | | |
| WO | 2020162816 A1 | 8/2020 | | |
| WO | 2021041210 A1 | 3/2021 | | |

OTHER PUBLICATIONS

Communication from the European Patent Office dated Oct. 30, 2024 in related EP application No. 21 725 515.7, including examined claims 1-17.

Mahadi Hasan et al, "A review of modern advancements in micro drilling techniques", Journal of Manufacturing Processes, vol. 29, 2017, pp. 343-375, Elsevier, Amsterdam, Netherlands.

Written Opinion and International Search Report of the International Searching Authority in PCT/EP2021/064755 dated Dec. 9, 2021.

Third Party Observation mailed Dec. 9, 2024, in related EP application No. 21730870, and pending claims 1-15.

Office Action from the Chinese Patent Office dispatched Apr. 26, 2025, in related CN application No. 202180036887.8, and translation thereof.

English-language Search Report dated Nov. 27, 2023 in Chilean application No. 202203262.

Applicant's reply filed Nov. 17, 2025, in counterpart EP application No. 21 730 870.9, in response to EPO Communication mailed Aug. 8, 2025, including argument and amended claims 1-13.

Examination Report from the European Patent Office dated Aug. 8, 2025, in counterpart EP application No. 21 730 870.9, including grounds for rejection and examined claims 1-15.

(56)　　　　　　References Cited

OTHER PUBLICATIONS

Handbook of Thermal Engineering vol. 4 Power Plant Chemistry, Xi'an Institute of Thermal Engineering, Ministry of Energy, Water Conservancy and Electric Power Press (1993) p. 615, and English translation thereof.

Office Action and Search Report from the Chinese Patent Office dated Jun. 23, 2025, in counterpart CN application No. 202180039733.4, and translation thereof.

Office Action and Search Report from the Chinese Patent Office dated Nov. 3, 2025, in related CN application No. 202180036887.8, and translation thereof.

Regeneration of Waste Lubricating Oil, Information Office of the Comprehensive Research Institute of the Academy of Petrochemical Sciences, Fuel Chemical Industry Publishing House (1974), p. 74, and English translation thereof.

Waste Oil Recycling Process, edited by Li Jiwu et al., China Railway Publishing House (1984) pp. 153-154, and English translation thereof.

Communication from the European Patent Office dated Feb. 23, 2026, in counterpart EP application No. 21 730 870.9, including Third Party Observation and pending claims 1-13.

* cited by examiner

S1 Providing filter material

S2 Producing filter body

S3 Impregnating

OIL PURIFICATION FILTER

CROSS-REFERENCE

This application is the U.S. National Stage of International Application No. PCT/EP2021/064755 filed on Jun. 2, 2021, which claims priority to German patent application no. 10 2020 207 112.8 filed on Jun. 5, 2020.

TECHNICAL FIELD OF THE INVENTION

The present invention relates to an oil purification filter and to an oil purification system comprising such an oil purification filter and to a method for producing an oil purification filter.

BACKGROUND

Purification of contaminated oil, such as for example industrial oil, lubrication oil, hydraulic oil or processing oil, is important for the possibility to reuse the oils and therefore an important factor for the environmental future and the limited nature resources of oils. Filtering of oil through different types of filters is often used for the purification of contaminated oil. However, the efficiency of these filtering techniques is not always adequate. Furthermore, there may be a risk that valuable components in the oil such as additives will also be removed by the filtering.

There is a need to improve the possibility to reuse oils.

SUMMARY

It is therefore one non-limiting object of the present teachings to disclose techniques for improving an oil purification filter.

It is another non-limiting object of the present teachings to disclose techniques for improving an oil purification system which can be used for cleaning oil used in a technical equipment, such as for example gear boxes and hydraulic systems.

According to one aspect of the present teachings, an oil purification filter may comprise a filter body which is, at least in a first part (portion) of a volume of the filter body, impregnated with a separation aid, which separation aid composition is substantially insoluble in a contaminated oil to be purified by said oil purification filter because of its polar properties and which separation aid will, by chemical interactions, adsorb/absorb contaminating solids and/or dissolved impurities in the oil to be purified.

According to another aspect of the present teachings, a method for producing an oil purification filter may comprise:

providing a filter material;

impregnating at least a part (portion) of the filter material with a separation aid, which separation aid is substantially insoluble in a contaminated oil to be purified by said oil purification filter because of its polar properties and which separation aid will, by chemical interactions, adsorb/absorb contaminating solids and/or dissolved impurities in the oil to be purified; and producing a filter body from said filter material.

According to another aspect of the present teachings, an oil purification filter may comprise a filter body which is, at least in a first part (portion) of a volume of the filter body, impregnated with a separation aid, which separation aid is substantially insoluble in a contaminated oil to be purified by said oil purification filter because of its polar properties and which separation aid will, by chemical interactions, adsorb/absorb contaminating solids and/or dissolved impurities in the oil to be purified, wherein said oil purification filter is produced by the above-described method.

According to another aspect of the present teachings, an oil purification system comprising an oil purification filter as defined above is provided, wherein the oil purification system is configured to be connected to a technical equipment which utilizes oil such that the oil is circulated through the oil purification filter for the purification of the oil.

According to the present teachings, a very effective oil purification filter is provided. Even very small contamination particles, as small as micro and nano particles, are caught in the filter thanks to the separation aid which is impregnated in at least a part (portion) of the filter volume. The separation aid is designed to, by chemical interactions, adsorb/absorb contaminating solids. The actual filter pore dimensions can in this filter be provided large enough to allow certain additives to pass therethrough. Consequently, additives that are valuable to keep in the oil can be kept in the oil during filtration; i.e. such additives will not be caught in the filter. This is a great advantage compared to other types of fine filters in which valuable additives also might be filtered out from the oil.

In some embodiments of the present teachings, the oil purification filter is configured to clean a contaminated oil that comprises at least one specific additive and the separation aid is designed (formulated) to be passive, i.e. not attracting, with respect to said at least one specific additive in the contaminated oil to be purified. As a result, valuable additives can be kept in the oil; i.e. they will not be caught in the oil purification filter during purification of the oil.

In some embodiments of the present teachings, the filter body comprises a network of cellulose fibers and the separation aid is bonded to the cellulose fibers in at least the first part (portion) of a volume of the filter body. Because the separation aid can be effectively bonded to a network of cellulose fibers, an effective impregnation is achieved.

In some embodiments of the present teachings, the total volume of the filter body comprises at least a first part (portion) and a second part (portion) of the volume of the filter body. The first part is provided (arranged, disposed) between an inlet of the filter and the second part; the second part is provided (arranged, disposed) between an outlet of the filter and the first part. In such embodiments, only the first part of the volume is impregnated with the separation aid. This reduces the risk that separation aid might come loose from and pass through the filter together with the oil.

In some embodiments of the present teachings, the filter body comprises a number (plurality) of layers of sheets of filter material which are provided (disposed, superposed) on each other as a stack of separate sheets and/or as a cylinder with one or more sheets wound in layers around an inner cylinder. The layers of sheet of filter material comprise a network of cellulose fibers; at least some of the sheets of filter material or at least one of the sheets or at least a part of at least one sheet further comprise(s) separation aid which is bonded to the cellulose fibers. The interfaces between individual sheets may foster retention of the separation aid within individual sheets and therefore minimize the risk that separation aid would come loose from and pass through the filter together with the oil.

In some embodiments of the present teachings, the oil purification filter is designed as a filter insert for use in a filter housing for purification of an oil. In such embodiments, the filter insert can easily be changed if needed.

In some embodiments of the method of the present teachings, the step of providing a filter material comprises providing a cellulose fiber filter material.

In some embodiments of the present teachings, the step of impregnating comprises applying the separation aid to a network of the cellulose fibers when the dryness of the cellulose fiber network is a suitable dryness for effective up-take of the separation aid onto and into the cellulose fibers due to their swollen state in water, wherein said suitable dryness is within 20-60% of the dry mass of the cellulose fibers to the total mass of the (wetted) cellulose fiber network. In such a dryness state, the separation aid will be bonded stronger to the cellulose fibres. The binding can be both by hydrogen bonds and by the separation aid being caught within the cellulose fibres when the cellulose fibres are drying and are collapsing after having had been in a wet swollen state.

In some embodiments of the present teachings, the step of producing a filter body from said filter material comprises providing (disposing, superposing) layers of sheets of filter material on each other by stacking separate sheets on each other and/or by winding one or more sheets in layers around an inner cylinder, wherein at least one of said sheets or at least a part (portion) of one sheet is impregnated with the separation aid.

In some embodiments of the present teachings, the step of impregnating at least a part (portion) of said filter material is performed at least partly during the step of producing the filter body, wherein the step of producing the filter body comprises:

- forming sheets of the filter material, wherein the filter material is a cellulose fiber filter material;
- impregnating at least one of said sheets with separation aid; and
- stacking said sheets onto each other and/or winding said sheets around an inner cylinder to form the filter body, wherein said step of forming the sheets comprises suspending the cellulose fiber filter material in water to form a cellulose fiber suspension comprising cellulose fibers in a singularized, swollen state, and then de-watering the cellulose fiber suspension, using gravity or gravity and vacuum, and possibly, but not necessarily, pressing the de-watered cellulose fiber suspension, wherein said de-watering and possibly pressing is performed to a degree such that the sheet(s) has (have) a suitable dryness for effective up-take of the separation aid onto and into the cellulose fibers due to their swollen state in water, wherein the suitable dryness is 20-60% of the dry mass of the cellulose fibers to the total mass of the cellulose fiber network (i.e. the mass of the dry mass of the cellulose fibers plus the mass of the water absorbed by the cellulose fibers), and wherein the step of impregnating is performed on at least one of said sheets when the suitable dryness of the sheets is achieved.

In some embodiments of the present teachings, the step of impregnating comprises (i) soaking at least a part (portion) of the filter material in the separation aid or in a solution of separation aid and water and/or (ii) spraying at least a part (portion) of the filter material with a separation aid or with a solution of separation aid and water and/or (iii) flowing the separation aid mixed with an oil over at least a part (portion) of the filter material.

In some embodiments of the present teachings, the method further comprises the step of drying the impregnated filter material to 90-100% of the dry mass of the cellulose fibers to the total mass of the cellulose fiber network after impregnating with the separation aid.

In some embodiments of the present teachings, the step of impregnating comprises impregnating only a first part (portion) of the filter material; the step of producing a filter body comprises combining the first part (portion) of the filter material which has been impregnated with the separation aid and at least a second part (portion) of filter material which is not impregnated with separation aid, wherein the first part is provided (arranged, disposed) between an inlet of the filter and the second part and the second part is provided (arranged, disposed) between an outlet of the filter and the first part.

In some embodiments of the oil purification system according to the present teachings, the oil purification system comprises a filter housing in which said oil purification filter is removably provided (arranged, disposed); an inlet of the filter is connected to an inlet of the filter housing and an outlet of the filter is connected to an outlet of the filter housing. The oil purification system further comprises an inlet fluid connection connected to the inlet of the filter housing, an outlet fluid connection connected to the outlet of the filter housing such that a fluid can be transferred into the inlet of the filter housing via the inlet fluid connection, through the filter housing and through the oil purification filter and further out from the filter housing through the outlet of the filter housing and further through the outlet fluid connection.

In some embodiments of the present teachings, the oil purification system further comprises at least one oil condition monitoring sensor for measuring a value indicative of a condition of the oil being purified in said oil purification system. Thereby, values from the sensor can indicate whether or not the oil purification filter needs to be changed.

DETAILED DESCRIPTION OF EMBODIMENTS

Figures 1A, 1B:
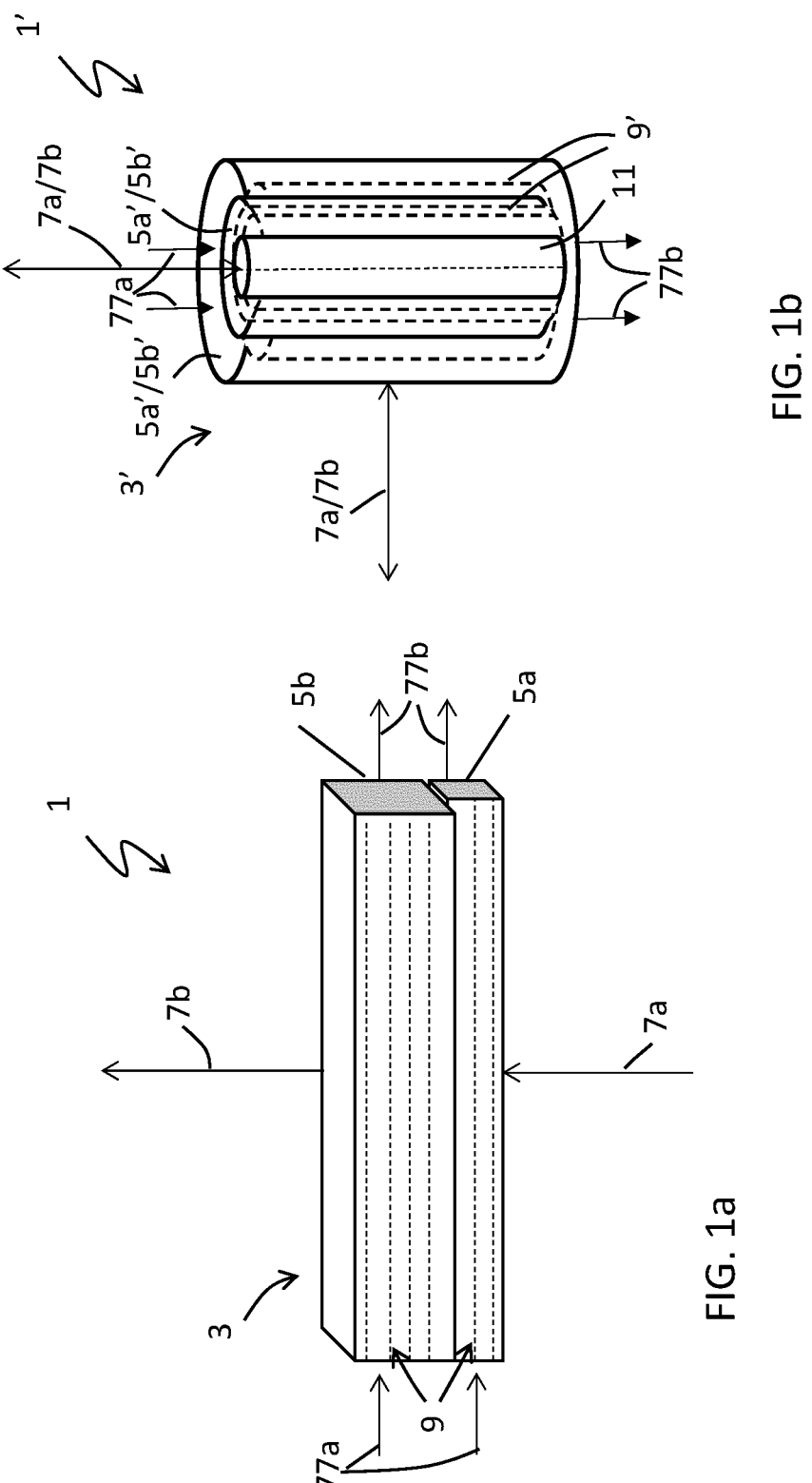
FIGS. 1a-1b respectively show schematically two different general principles of an oil purification filter according to embodiments of the present teachings.
Figure 1D:
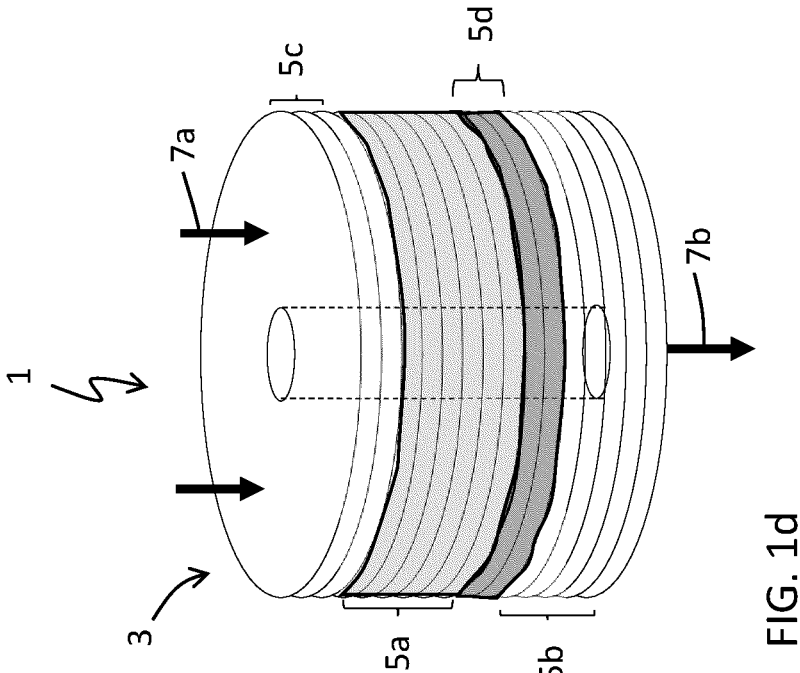
FIGS. 1c-1g respectively show schematically five different, more detailed examples, of oil purification filters according to embodiments of the present teachings.
Figure 1C:
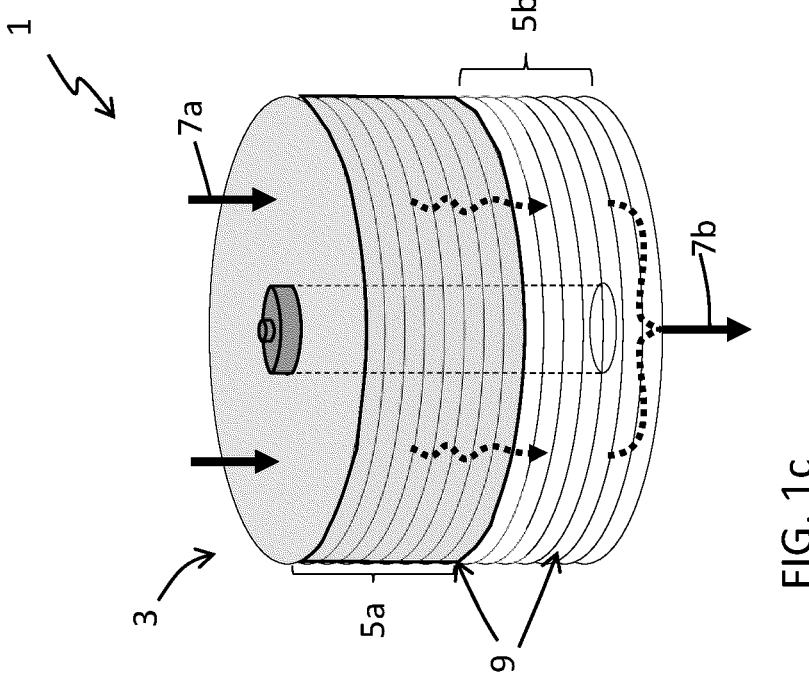
Figure 1F:
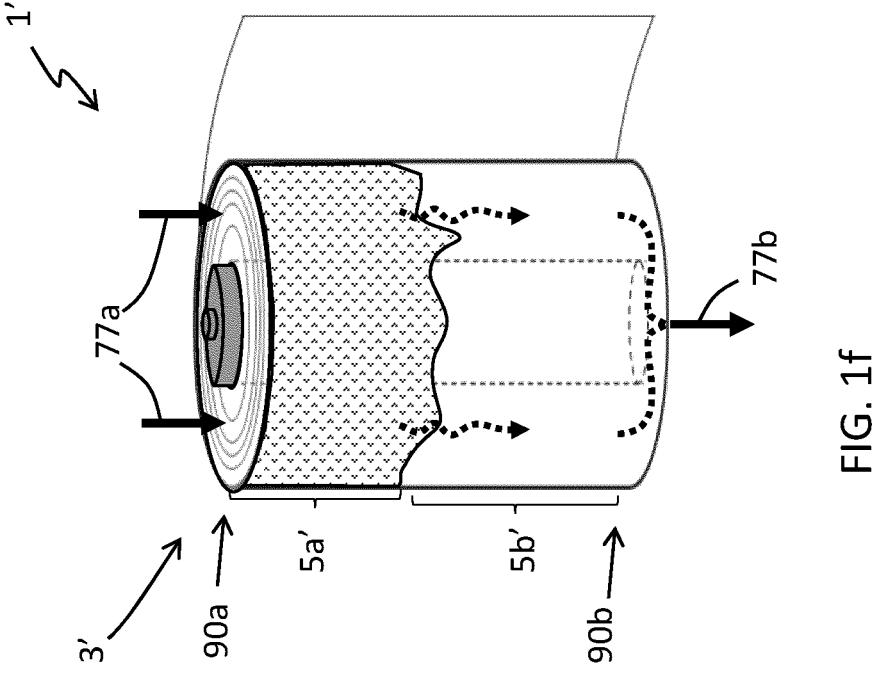

FIGS. 1a and 1b respectively show schematically two different general principles of an oil purification filter 1; 1' in accordance with some embodiments of the present teachings. In FIGS. 1c and 1d the basic principle is the same as shown in FIG. 1a; in FIGS. 1e and 1f the basic principle is the same as shown in FIG. 1b. FIG. 1g shows a filter 1" comprising a mix of the two basic principles as shown in FIGS. 1a and 1b. The oil purification filter can be configured for cleaning contaminated oil, such as for example industrial oil, lubrication oil, hydraulic oil or processing oil for example used in gear boxes, hydraulic systems, automotive equipment and construction equipment.

The filter 1; 1'; 1" comprises a filter body 3; 3'; 3" that is, in at least in a first part (portion) 5a; 5a' of the volume of the filter body 3; 3'; 3", impregnated with a separation aid. Both embodiments shown in FIGS. 1a and 1b include the first part 5a, 5a' of the filter body 3, 3' that comprises separation aid which has been provided to (in) the filter such that the separation aid is bonded to the filter, herein also referred to as "impregnated with separation aid". A second part (portion) 5b; 5b' of the filter body 3; 3' comprises in these embodiments no separation aid; i.e. the second part 5b; 5b' is not impregnated with separation aid. However, the impregnation with separation aid can also be provided throughout the entire filter body volume in other embodiments of the present teachings. By only impregnating the first part 5a; 5a' of the filter body volume 3; 3', the risk that separation aid will come loose (separate) from and pass through the filter together with the filtered oil can be minimized, which may be advantageous.

The relationship between the volumes of the first and second parts 5a; 5a', 5b; 5b' can be varied. In some embodiments of the present teachings, the volume of the second part 5b; 5b' is larger than the volume of the first part 5a, 5a'. This is however not necessary.

The first part 5a; 5a' can be provided between an inlet 7a of the filter 1; 1'; 1" and the second part 5b; 5b'; the second part 5b; 5b' can be provided between an outlet 7b of the filter 1; 1'; 1" and the first part 5a; 5a'. In some embodiments only the first part 5a; 5a' or only the second part 5b; 5b' of the volume is impregnated with the separation aid.

The filter body 3; 3'; 3" can comprise more than two parts. The part which is referred to as the first part 5a; 5a' need not be provided closest to the inlet 7a of the filter 1; 1'; 1" in all embodiments but one or more other parts of the filter body can be provided between the first part 5a; 5a' and the inlet 7a in some embodiments. Similarly, the part referred to as the second part 5b; 5b' need not to be provided closest to the outlet 7b of the filter 1; 1'; 1" in all embodiments; however, one or more other parts of the filter body volume may be provided between the second part 5b; 5b' and the outlet 7b. The first and second parts 5a, 5b; 5a', 5b' may also shift (exchange) places such that the first part 5a, 5a' is provided closer to the outlet 7b of the filter than the second part 5b; 5b' is and the filter body 3; 3'; 3" can also in some embodiments comprise only one part.

Different parts of the filter body 3; 3'; 3' may exhibit different properties, such as: (i) impregnated with separation aid or not, (ii) impregnated to different degrees with separation aid, (iii) different porosity and/or density of the filter, (iv) different material of the filter, etc. The different parts can in some embodiments of the present teachings diffuse into each other; i.e. there need not be a distinct border between the different parts of the filter. This may for example be the case in the examples in which the filter 1; 1'; 1" is impregnated with separation aid after a filter body 3; 3'; 3" has been produced in the manner described below with regard to FIG. 4.

The separation aid composition is substantially insoluble in the contaminated oil to be purified by said oil purification filter because of its polar properties. Furthermore, the separation aid will, by chemical interactions, adsorb/absorb contaminating solids and/or dissolved impurities in the oil to be purified.

The separation aid which is used in the present teachings has in some embodiments a density that is different from that of the oil to be purified. The separation aid attracts impurities in the oil when oil and separation aid come into contact.

The use of a separation aid, which also may be called a chemical booster or separation booster herein, for capturing impurities in contaminated oil has been described before, see for example WO 2018/199839. Here the liquid separation booster/aid is added to the oil and mixed therewith; impurities in the oil will be captured by the separation aid and will accumulate in a phase which can be separated, for example, in a bottom phase.

As was noted above, the separation aid will, by chemical interactions, adsorb/absorb contaminating solids and/or dissolved impurities in the contaminated target oil.

The separation aid is preferably liquid at the temperature at which the step of impregnation is carried out. The separation aid composition should be substantially insoluble in the contaminated target oil, so that it will form a two-phase liquid mixture when mixed with the contaminated oil. The liquid separation aid can also have a density different from that of the contaminated oil to be purified.

The separation aid is not soluble in the contaminated target oil because of its polar properties and will, through chemical interactions (hydrophilic, hydrophobic, and/or charge interactions), adsorb/absorb unwanted solid and/or dissolved impurities in the contaminated target oil.

The liquid separation aid/booster for use in the present teachings can generally be made up based on the following components: a) a polar polymer; b) a hydrotrope/solubilizer; and c) a co-tenside.

Suitable separation aids having the properties described above, which can be used in processes according to the present teachings, may e.g. be constituted (formulated) as a composition comprising a mixture of (a) one or more polar polymers such as polyethylene glycols, polypropylene glycols or similar polyalkylene glycols, and (b) one or more organic surface active components having nonionic, anionic, cationic and amphoteric properties capable of increasing the solubility of solid and/or dissolved impurities in the separation aid.

One example of a separation aid which can be used with the present teachings comprises: a) at least one polar polymer that is not soluble in oil and has a higher density than the oil, such as a polyethylene glycol having an average molecular weight of 190-210 g/mole, e.g., Carbowax® PEG 200 (Dow Chemical Company); b) at least one surface active hydrotrope/solubilizer, such as one or more anionic sulfonic acids, phosphate ester-based substances or nonionic surfactants from the poly-glycoside family, such as Simulsol SL 4, Simulsol SL 7 G and Simulsol AS 48 (Seppic, Air Liquide group); and c) at least one amphoteric co-surfactant, such as a propionate type, e.g., Ampholak YJH-40 (Akzo Nobel) which is a sodium caprylimino dipropionate.

The separation aid may further exhibit a sufficiently big difference in polarity compared to the polarity of at least one specific additive in the contaminated oil to be purified such that the at least one specific additive is not soluble in the separation aid.

In some embodiments of the present teachings, the oil purification filter 1; 1'; 1" is configured for cleaning a contaminated oil comprising at least one specific additive and said separation aid is designed (formulated) to be passive, i.e. not attracting, with respect to said at least one specific additive in the contaminated oil to be purified. Thereby, at least this specific additive can travel through the filter 1; 1'; 1" together with the clean oil. The sizes of the filter pores are in some embodiments of the present teachings dimensioned such that valuable additives can pass through the filter. The use of the separation aid for impregnating at least a first part (portion) of the filter will ensure that other contaminations will be caught in the filter even if the sizes of the filter pores are somewhat bigger. However, the separation aid will not attract this specific additive and will thereby let it pass through the filter. As a result, valuable additives can be kept in the filtered oil while small contamination particles still can be filtered out from the oil. Of course, said separation aid can be designed (formulated) to be passive with respect to more than one specific additive. Furthermore, an oil, which is to be used in a technical equipment and which should be filtered in the filter 1; 1'; 1" according to the present teachings, can be designed (formulated) to comprise suitable additives which are designed or chosen in relation to the features of the separation aid provided to (impregnated in) the filter 1; 1'; 1".

The filter body 3; 3'; 3" can be a depth filter and may comprise cellulose fibers. In some embodiments of the present teachings, a network of cellulose fibers is provided in the filter body 3; 3'; 3". The separation aid can be bonded to the cellulose fibers in at least the first part 5a; 5a' or at least the second part 5b; 5b' of a volume of the filter body 3; 3'; 3".

The impregnation of separation aid into the filter material can be done in different ways. A method for producing a filter according to the present teachings is described in further detail below in relation to FIG. 3. However, a part of the filter material can be soaked in the separation aid (possibly in a solution of separation aid and water), or can be sprayed with the separation aid (possibly separation aid and water) or the separation aid mixed with oil can be flowed over the filter material to perform the impregnation.

In order to achieve a stronger bond between the cellulose fibers and the separation aid, the cellulose fibers can be wetted before or during the impregnation. Optionally a bonding agent could also be added to provide an even stronger and possibly tailor-made bond between the cellulose fibers and the separation aid. In one embodiment the separation aid is applied to the filter material during a sheet forming process in which a cellulose fiber suspension is processed into sheets. By applying the separation aid during this process, i.e. during a stage in the process in which the cellulose fibers are still wet and before a final filter product is achieved, the bond between the separation aid and the cellulose fibers will be stronger. Wet cellulose fibers are swollen and separation aid can be caught within the fibers when the cellulose fibers are dried and their swollen state collapses. The separation aid may also be bonded to the cellulose fibers by hydrogen bonds. Hereby, in some embodiments of the present teachings, the bonding between the separation aid and the cellulose fibers has been provided by applying the separation aid to the cellulose fibers during a process for forming the cellulose fibers into a filter body at a stage in the process in which the dryness is 20-60% of the dry mass of the cellulose fibers to the total mass of the cellulose fiber network, which is the dry mass of the cellulose fibers plus the mass of the water that is absorbed in the cellulose fiber network.

In some embodiments of the present teachings, the filter body 3; 3'; 3" comprises a number of layers of sheets 9; 9' of filter material which are provided (laid, superposed) on each other as a stack of separate sheets 9, as shown in FIG. 1a, and/or as a cylinder with one or more sheets 9' wound in layers around an inner cylinder 11, as shown in FIG. 1b. Each of the layers of sheets 9; 9' of filter material comprise a network of cellulose fibers and at least some of the sheets 9; 9' or at least one sheet or at least a part of a sheet of filter material further comprise(s) separation aid which is bonded to the cellulose fibers. The interfaces between individual sheets 9; 9' will aid in retaining the separation aid within the individual sheets 9; 9'.

The filter body can for example comprise a cellulose fiber material having a density without bonded separation aid within the range of 100-600 kg cellulose/$m^3$. With separation aid bonded to 50% in this filter material, the density of the filter body would be within the range of 150-900 kg/$m^3$. If instead talking about the basis weight of a suitable cellulose filter, it can for example be within the range of 50-1500 kg cellulose/$m^3$ for filter material without bonded separation aid; with 50% bonded separation aid this would be within the range of 75-2250 kg/$m^3$.

As was mentioned above, FIGS. 1a and 1b respectively show two different general principles of a filter 1; 1'; 1" according to the present teachings, while FIGS. 1c-1g respectively show more detailed examples of filters according to the present teachings. In FIGS. 1c and 1d the basic principle is the same as shown in FIG. 1a and therefore their reference numbers correspond to the reference numbers of FIG. 1a; in FIGS. 1e and 1f the basic principle is the same as shown in FIG. 1b and therefore their reference numbers correspond to the reference numbers of FIG. 1b. FIG. 1g shows a filter 1" comprising a mix of the two basic principles as shown in FIGS. 1a and 1b. FIGS. 1a-1g are now described in order in more detail.

FIG. 1a shows a filter 1 comprising a filter body 3 having two parts, which will be called a first part (portion) 5a and a second part (portion) 5b. In other embodiments according to the present teachings, only one part need be provided or more than two parts can be provided. The parts can also diffuse into each other. However, in some embodiments of the present teachings, only one of the parts, possibly the first part 5a or the second part 5b, is impregnated with separation aid as described above. The impregnation can be provided during production of the filter as described in relation to FIG. 3 or after the production of the filter as described in relation to FIG. 4.

The filter body 3 may comprise a network of cellulose fibers, in which case the separation aid is bonded to the cellulose fibers in at least a first part 5a or a second part 5b of the filter body 3.

The filter 1 comprises an inlet 7a and an outlet 7b whereby the filter body 3 is provided between the inlet 7a and the outlet 7b such that a fluid (e.g., contaminated oil) to be filtered in the filter 1 is received via the inlet 7a into the filter body 3 and is transferred out (discharged) from the filter 1 via the filter outlet 7b. In this example the filter body 3 may comprise a number of stacked layers of sheets 9 of filter material. At least some of the sheets or at least one sheet may be impregnated with separation aid as described above and will be further described below. If the filter body 3 comprises stacked layers of sheets 9, the fluid to be filtered is transferred across (passes through) the sheets 9 when the fluid enters via the inlet 7a and exits through outlet 7b. However, according to the present teachings, filtering along sheets 9 of filter material is also possible. This is schematically illustrated in FIG. 1a by the alternate inlet 77a and outlet 77b and will be further described below in relation to FIGS. 1f and 1g. However, in this case there will be no difference between the first part 5a and the second part 5b.

FIG. 1b shows a filter 1' comprising a filter body 3' in the form of a cylinder having two parts, which will be called a first part 5a' and a second part 5b'. The filter 1' comprises an inlet 7a and an outlet 7b whereby the filter body 3' is provided between the inlet 7a and the outlet 7b such that a fluid to be filtered in the filter 1' is received via the inlet 7a into the filter body 3' and is transferred out (discharged) from the filter 1' via the filter outlet 7*b*. As can be seen in FIG. 1*b*, the inlet 7*a* and the outlet 7*b* can change places and hereby also the first part 5*a'* and the second part 5*b'* can change places. That is, fluid to be filtered can either be received through a mantel (outermost) surface of the cylindrical filter body 3' and then transferred out (discharged) from a center of the filter body 3' (most likely) or fluid to be filtered can be received into the center of the cylindrical filter body 3' and then transferred out (discharged) via a mantel (outermost) surface. Both alternatives are schematically illustrated in FIG. 1*b*.

Two parts 5*a'*, 5*b'* are shown in FIG. 1*b*, but again only one part need be provided according to the present teachings or more than two parts can be provided. The parts can also diffuse into each other. However, in some embodiments of the present teachings, only one of the parts, possibly the first part 5*a'* or the second part 5*b'*, is impregnated with separation aid as described above. The impregnation can be provided during production of the filter as described in relation to FIG. 3 or after the production of the filter as described in relation to FIG. 4.

The filter body 3' may comprise a network of cellulose fibers, whereby the separation aid is bonded to the cellulose fibers in at least a first part 5*a'* or a second part 5*b'* of the filter body 3'. In this example the filter body 3 may comprise a number of wound layers of sheets 9' of filter material. At least some of the sheets or at least one sheet or at least a part of at least one sheet may be impregnated with separation aid as described above and will be further described below. If the filter body 3' comprises wound layers of sheets 9', the fluid to be filtered is transferred across (passes through) the sheets 9' when the fluid enters via the inlet 7*a* and exits through outlet 7*b*. However, according to the present teachings, filtering along sheets 9' of filter material is also possible. This is schematically illustrated in FIG. 1*b* by the alternate inlet 77*a* and outlet 77*b* and will be further described below in relation to FIGS. 1*f* and 1*g*.

The two basic principles as shown in FIGS. 1*a* and 1*b* can be combined and embodied in different ways as will be exemplified in the examples shown in FIGS. 1*c*-1*g*. In FIG. 1*c* a filter 1 comprises a filter body 3 having a number of stacked layers of sheets 9. The sheets 9 are in this embodiment circular and the filter body 3 thus forms a cylindrical shape. The filter 1 comprises an inlet 7*a* and an outlet 7*b* whereby the filter body 3 is provided between the inlet and the outlet 7*a*, 7*b*. The filter body 3 comprises a first part 5*a* which is impregnated with separation aid and a second part 5*b* which is not impregnated with separation aid. The filtering is provided across (through) the sheets 9.

FIG. 1*d* is almost the same as the filter 1 as shown in FIG. 1*c* and merely illustrates that there may be more than two parts and that different parts of the filter body 3 may have different properties. In the example of FIG. 1*d*, a first part 5*a* is provided which is impregnated with separation aid and a second part 5*b* is provided which is not impregnated with separation aid. However, two additional parts are also provided: one part 5*c* which in this example is not impregnated with separation aid and is provided between the inlet 7*a* and the first part 5*a* and one part 5*d* which is impregnated to another degree (i.e. comprises a larger or smaller proportion of separation aid) than the first part 5*a* and which is provided in between the first part 5*a* and the second part 5*b*. Other properties of the different parts 5*a*, 5*b*, 5*c*, 5*d* can also be varied, such as the porosity of the filter, the density of the filter, the degree of impregnation and the filter material. The number and order of different parts 5*a*, 5*b*, 5*c*, 5*d* in the filter body 3 can hereby be varied.

Figure 1E:
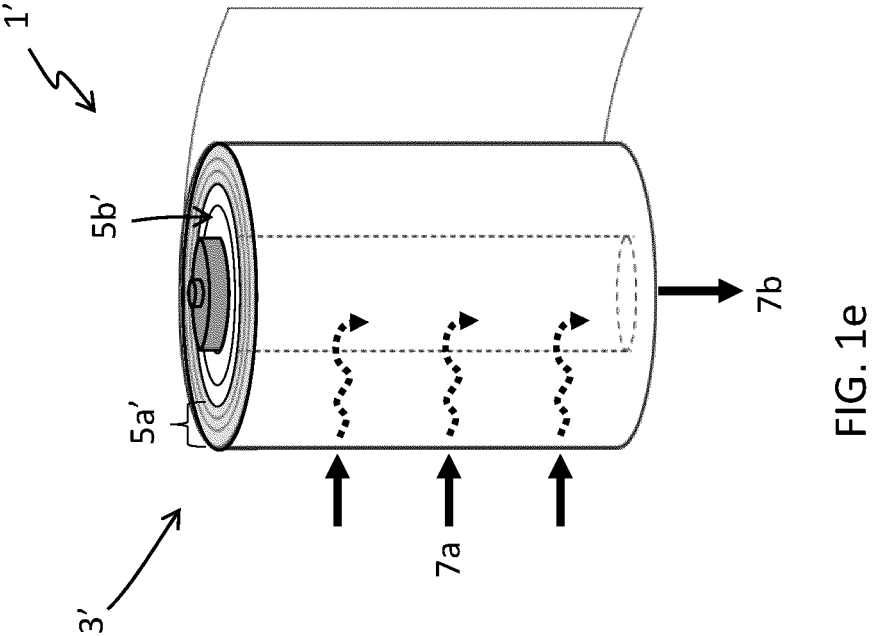
Figure 1G:
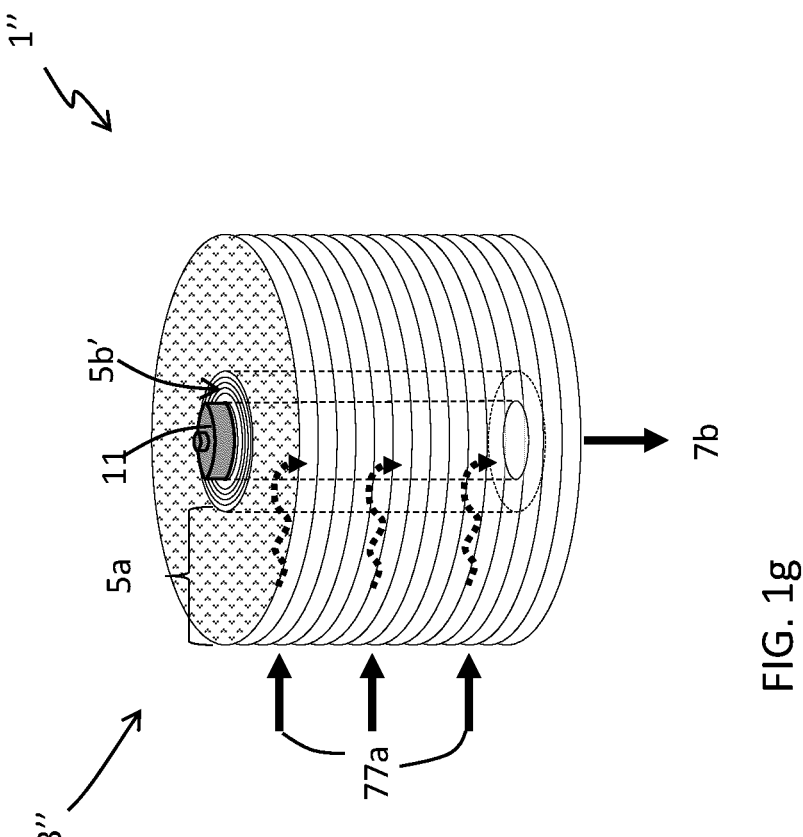

FIG. 1*e* shows a filter 1' comprising a filter body 3' having one or more sheets 9' wound in layers around an inner cylinder 11 according to the basic principle as shown in FIG. 1*b*. In this example an inlet 7*a* of the filter is provided via a mantel (outermost) surface of the cylindrical filter body 3' and an outlet 7*b* is provided in a center of the filter body 3'. The filter body 3' comprises a first part 5*a* which is impregnated with separation aid and a second part 5*b* which is not impregnated with separation aid. More parts can be provided as described above and said parts can exhibit different properties, such as different porosity, different density, different filtering material and different degree of impregnation of separation aid.

All the examples discussed thus far involve filtration across (through) sheets 9, 9' of filter material. However, according to the present teachings, filtration along sheets 9, 9' of filter material may also be provided. This is schematically illustrated and was discussed above in relation to FIGS. 1*a* and 1*b* by the alternate inlet and outlet 77*a*, 77*b*. Examples in which filtration along filter sheets 9, 9' are shown in FIGS. 1*f* and 1*g*.

FIG. 1*f* shows a filter 1' comprising a filter body 3' having one or more sheets 9' wound in layers around an inner cylinder 11 according to the basic principle as shown in FIG. 1*b*. In this example an inlet 77*a* is provided at a first end 90*a* of the cylindrical filter body 3' such that fluid will flow predominantly along (parallel to) the sheets 9' and an outlet 77*b* is provided at a second end 90*b* of the cylindrical filter body 3'. A first part 5*a'* of the filter body 3' is impregnated with a separation aid. This can either be done during production of the filter material by only impregnating a portion of the sheets 9' to be wound or instead after production of the filter body 3' according to the flow chart of FIG. 4. Another alternative would be to produce two filter bodies 3' with wound sheets of filter material whereby one of them is impregnated with separation aid and the other is not and then combining the two filter bodies 3'. There may be a decreased risk of clogging and stoppages in the filter when the filtering is performed along the layers of filter material instead of across (through) the layers. This may be advantageous. There also may be less risk that pores of the filter will be clogged by components in the fluid to be filtered.

FIG. 1*g* shows a filter 1" in which filtering along sheets 9 and filtering across (through) sheets 9' have been combined in the same filter 1". The filter 1" comprises a filter body 3" having a first part 5*a* which is impregnated with separation aid and which is provided as sheets 9 of filter material which are stacked onto each other. The filter 1" comprises an inlet 77*a* which will provide (supply) the fluid to be filtered into the filter body 3" such that the fluid will flow along the filter sheets 9. The filter sheets 9 have in this embodiment an annular form and they enclose an inner part of the filter body 3" which is a second part 5*b'* that is in the form of one or more sheets 9' wound around an inner cylinder 11. Hereby the fluid being filtered will enter the second part 5*b'* via a mantel (outermost) surface of the second part 5*b'* and then the fluid will flow across (through) the sheets 9' of the second part 5*b'* whereafter it will exit the filter 1" via an outlet 7*b* in the center. The second part 5*b'* is in this example not impregnated with separation aid. There may of course be more combinations of parts which are impregnated or not and which filter along the sheets of filter material or across (through) the sheets of filter material and filter material having different properties may be combined in any way.

Figure 2:
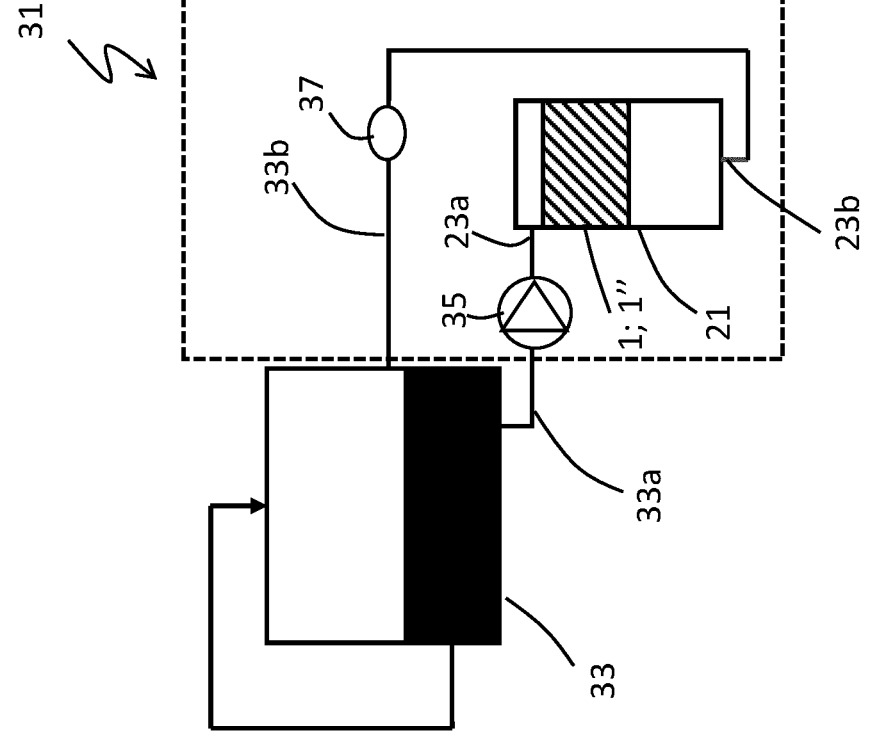
FIG. 2 shows schematically an industrial oil purification system according to one embodiment of the present teachings which is fluidly connected to a technical equipment that utilizes oil.

Oil purification filters 1; 1'; 1" according to the present teachings can be designed as a filter insert for use in a filter housing 21 for purification of an oil. FIG. 2 shows schematically an industrial oil purification system 31 according to one embodiment of the present teachings which is fluidly connected to a technical equipment 33 that utilizes oil.

Such an oil purification system 31 according to the present teachings comprises an oil purification filter 1; 1'; 1" according to the present teachings as described above.

Said oil purification system 31 is configured to be fluidly connected to a technical equipment 33 which utilizes oil such that the oil can be circulated through the oil purification filter 1; 1'; 1" for purification of the oil. Hereby oil used in the technical equipment 33 can be continuously cleaned in the oil purification system 31. Representative examples of technical equipment 33 that utilize oil can for example include industrial equipment, automotive equipment, construction equipment or metalworking machines using industrial oil, hydraulic oil and/or lubrication oil, such as for example gear boxes, hydraulic systems etc.

The oil purification system 31 can comprise a filter housing 21 in which said oil purification filter 1; 1 can be removably provided with an inlet 7a of the filter 1; 1'; 1" connected to an inlet 23a of the filter housing 21 and an outlet 7b of the filter 1; 1'; 1" connected to an outlet 23b of the filter housing 21. Said oil purification system 31 can further comprise an inlet fluid connection 33a connected to the inlet 23a of the filter housing 21, an outlet fluid connection 33b connected to the outlet 23b of the filter housing 21 and a pump 35 (a pump may be omitted if a pump in the connected technical equipment can be used) connected to at least one of the inlet and outlet fluid connections 23a, 23b such that a fluid can be transferred into the inlet 23a of the filter housing 21 via the inlet fluid connection 33a, through the filter housing 21 and through the oil purification filter 1; 1'; 1" and further out from filter housing 21 through the outlet 23b of the filter housing 21 and further through the outlet fluid connection 33b. Hereby oil used in the technical equipment 33 can be continuously transferred through the oil purification system 31 according to the present teachings and can be cleaned in the impregnated oil purification filter according to the present teachings.

In some embodiments of the present teachings, the oil purification system 31 further comprises at least one oil condition monitoring sensor 37 for measuring a value indicative of a condition of the oil being purified in said oil purification system 31. Due to the pressure drop over the oil purification filter 1, such a sensor is suitably positioned at a distance from the filter housing 21, i.e. not at a distance where it is affected by the pressure drop. Output from this oil condition monitoring sensor 37 can be used as an input for a decision whether or not to replace the oil purification filter 1; 1'; 1" in the filter housing 21 with a new one.

Figure 3:
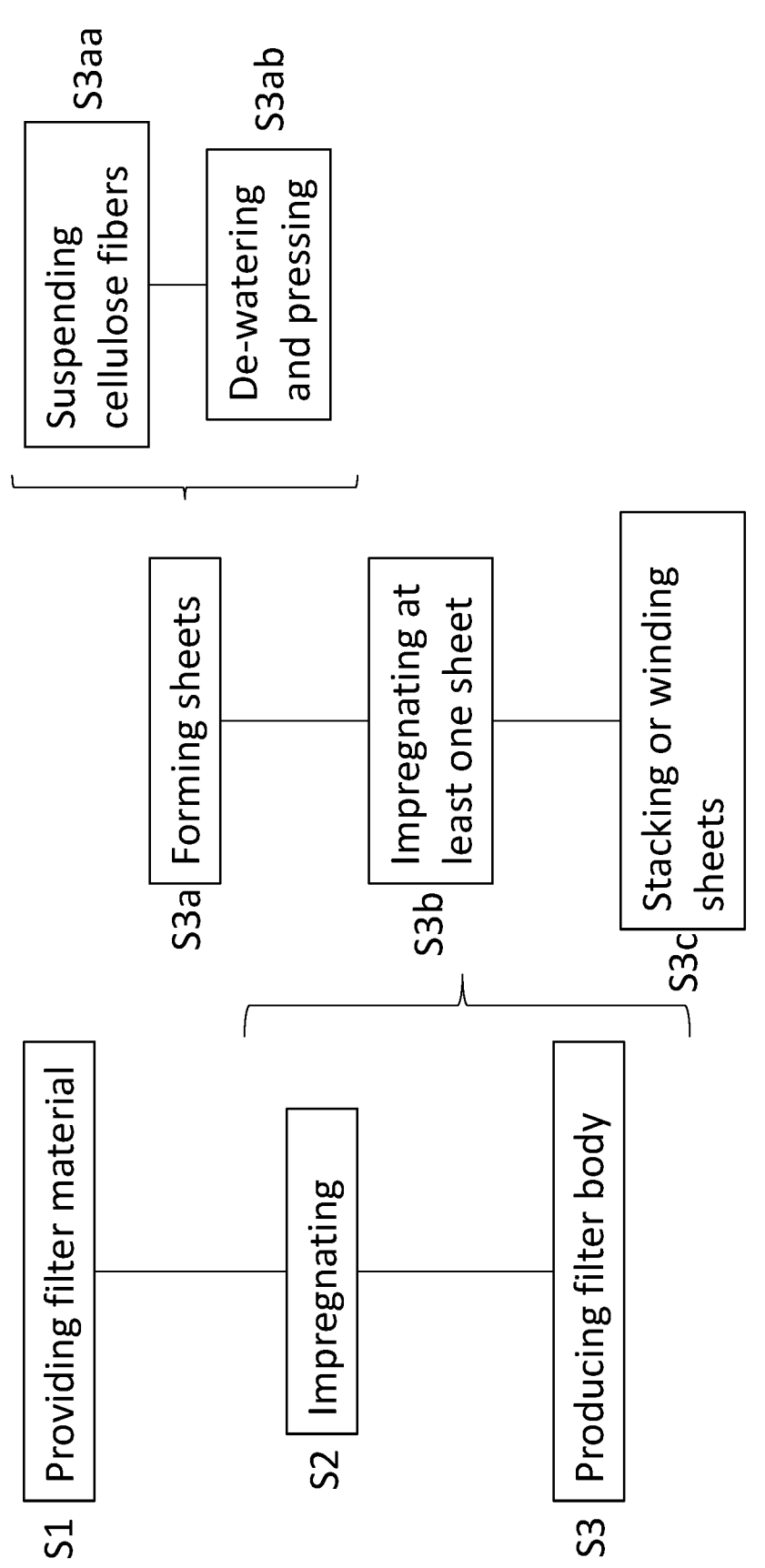
FIG. 3 is a flow chart showing method steps of a method according to one embodiment of the present teachings.

FIG. 3 is a flow chart showing method steps of a method for producing an oil purification filter 1; 1'; 1" comprising a filter body 3; 3'; 3" according to one embodiment of the present teachings. The steps of the method are described below with reference to FIG. 3.

S1: Providing a filter material. In some embodiments of the present teachings the filter material is a cellulose fiber filter material.

S2: Impregnating at least a part (portion) of said filter material with a separation aid, which separation aid composition is substantially insoluble in a contaminated oil to be purified by said oil purification filter because of its polar properties and which separation aid will, by chemical interactions, adsorb/absorb contaminating solids and/or dissolved impurities in the oil to be purified. In some embodiments of the present teachings, the step of impregnating (S2) comprises applying the separation aid to a network of the cellulose fibers when the dryness of the cellulose fiber network is a suitable dryness for effective up-take of the separation aid onto and into the cellulose fibers due to their swollen state in water, wherein said suitable dryness is within the range of 20-60% of the dry mass of the cellulose fibers to the total mass of the cellulose fiber network.

S3: Producing a filter body 3; 3'; 3" from said filter material. In some embodiments of the present teachings, the step of producing (S3) a filter body 3; 3'; 3" from said filter material comprises providing (disposing, superposing) layers of sheets 9; 9' of filter material on each other by stacking separate sheets 9 onto each other and/or by winding one or more sheets 9' in layers around an inner cylinder 11, wherein at least one of said sheets or at least a part of at least one sheet is impregnated with the separation aid. Stacking and winding can also be combined in the same filter as shown in FIG. 1g. The interfaces between individual sheets foster retention of the separation aid within individual sheets.

Figure 4:
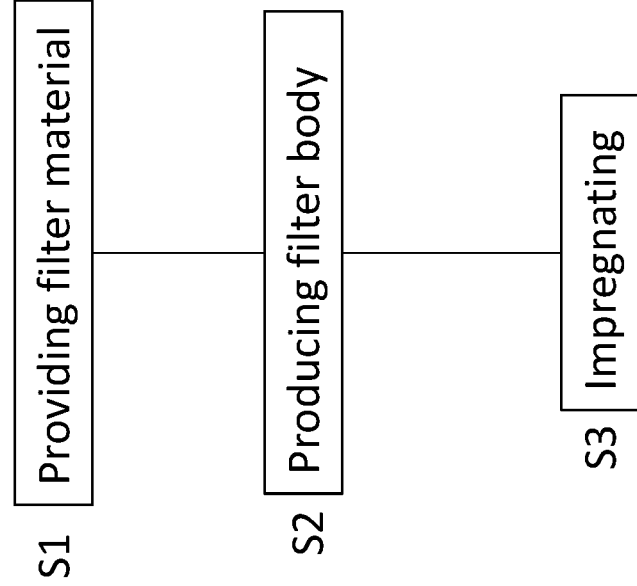
FIG. 4 is a flow chart of one embodiment of the present teachings.

In some embodiments, as shown in the flow chart of FIG. 4, the steps of impregnating (S2) and producing a filter body (S3) can be interchanged. Thereby a filter body can be produced before at least a part of it is impregnated. This impregnation can be provided by for example injecting separation aid via (using) a syringe or a pipette or the like into chosen parts of the filter body.

In some embodiments of the present teachings, the step of impregnating at least a part of said filter material (S2) is performed at least partly during the step of producing (S3) a filter body 3; 3'; 3", wherein the step of producing (S3) a filter body comprises:

S3a: Forming sheets of the filter material, wherein the filter material is a cellulose fiber filter material. The step of forming sheets (S3a) comprises suspending (S3aa) the cellulose fiber filter material in water to form a cellulose fiber suspension comprising cellulose fibers in a singularized, swollen state, and then de-watering (S3ab) the cellulose fiber suspension over for example a wire mesh, using gravity or gravity and vacuum, and possibly, but not necessarily, pressing (S3ab) the de-watered cellulose fiber suspension. The de-watering and possibly pressing (S3ab) is performed to a degree such that the sheet has a suitable dryness for effective up-take of the separation aid onto and into the cellulose fibers due to their swollen state in water, wherein the suitable dryness is within a range of 20-60% of the dry mass of the cellulose fibers to the total mass of the cellulose fiber network.

S3b: Impregnating at least one of or at least a part of one of said sheets with separation aid. The step of impregnating (S3b) is performed on at least one of or at least a part (portion) of one of said sheets when the suitable dryness of the sheets is achieved.

S3c: Stacking said sheets onto each other and/or winding said sheets around an inner cylinder 11 to form the filter body 3, 3'; 3".

The step of impregnating (S2, S3b) may comprise soaking at least a part (portion) of the filter material in the separation aid (or in a solution of separation aid and water) and/or spraying at least a part (portion) of the filter material with a separation aid (or separation aid and water) and/or flowing the separation aid mixed with an oil over at least a part (portion) of the filter material.

After the impregnation, the method may comprise a further step of drying the impregnated filter material to 90-100% of the dry mass of the cellulose fibers to the total mass of the cellulose fiber network after the impregnating. The drying can be performed at normal room temperature or at an elevated temperature, for example within the range of 80-120 degrees Celsius.

The step of impregnating (S2; S3b) may comprise impregnating only a first part (portion) 5a of the filter material and the step of producing (S3) a filter body may comprise combining the first part 5a of filter material which is impregnated with separation aid and a second part (portion) 5b of filter material which is not impregnated with separation aid, wherein the first part 5a is provided between an inlet 7a of the filter 1; 1'; 1" and the second part 5b and the second part 5b is provided between an outlet 7b of the filter 1; 1'; 1" and the first part 5a.

An oil purification filter 1; 1'; 1" which is produced by a method as described above is also provided according to the present teachings.

The invention claimed is:

1. An oil purification filter for purifying a contaminated oil, the filter comprising:
a filter body composed of a network of cellulose fibers, wherein:
the filter body has a first portion and a second portion,
at least the first portion is impregnated with a separation aid,
the separation aid is substantially insoluble in the contaminated oil because of polar properties of the separation aid,
the separation aid is formulated to adsorb/absorb contaminating solids and/or dissolved impurities in the contaminated oil by hydrophilic, hydrophobic, and/or charge interactions, and
the oil purification filter is configured as a filter insert mountable in a filter housing.

2. The oil purification filter according to claim 1, wherein the oil purification filter is formulated to allow at least one specific additive in the contaminated oil to pass through the filter.

3. An oil purification filter for purifying a contaminated oil, the filter comprising a filter body having a first portion and a second portion, at least the first portion being impregnated with a separation aid, the separation aid being substantially insoluble in the contaminated oil because of polar properties of the separation aid and the separation aid being configured to adsorb/absorb contaminating solids or dissolved impurities in the contaminated oil by chemical interactions;
wherein the filter body comprises a network of cellulose fibers and wherein the separation aid is bonded to the cellulose fibers in at least the first portion of the filter body;
wherein the first portion is provided between an inlet of the filter and the second portion and the second portion is provided between an outlet of the filter and the first portion and
wherein the second portion is not impregnated with the separation aid.

4. The oil purification filter according to claim 1, wherein the filter body comprises a plurality of sheets of filter material arranged in layers to form a stack and/or at least one sheet of the filter material wound in layers around an inner cylinder.

5. The purification filter according to claim 3, wherein the oil purification filter is configured as a filter insert mountable in a filter housing.

6. A method for producing an oil purification filter for purifying a contaminated oil, the method comprising:
providing a filter body that comprises a filter material composed of a network of cellulose fibers, the filter material having a first portion and a second portion;
impregnating only the first portion of the filter material with a separation aid, the separation aid being (i) a liquid at the temperature at which the impregnation is carried out, (ii) substantially insoluble in the contaminated oil because of polar properties of the separation aid and (iii) formulated to adsorb/absorb contaminating solids and/or dissolved impurities in the contaminated oil by hydrophilic, hydrophobic, and/or charge interactions; and
disposing the filter body in a filter housing in an orientation such that the first portion of the filter material is disposed between an inlet of the filter housing and the second portion of the filter material, and the second portion of the filter material is disposed between an outlet of the filter housing and the first portion of the filter material, wherein the second portion of the filter material is not impregnated with the separation aid.

7. The method according to claim 6, wherein prior to impregnating only the first portion of said filter material with the separation aid, the cellulose fiber network is brought into a swollen state by applying water to a dry mass of the network of cellulose fibers, and the dryness of the wetted network of cellulose fibers is then adjusted to a ratio of the dry mass of the network of cellulose fibers to the total mass of the wetted network of cellulose fibers that is 20-60%.

8. The method according to claim 7, wherein:
providing the filter body comprises stacking a plurality of sheets of the filter material to form layers and/or winding at least one sheet of the filter material in layers around an inner cylinder.

9. The method according to claim 6, wherein:
the step of impregnating only the first portion of said filter material at least partly occurs during the step of providing the filter body,
the step of providing the filter body further comprises:
forming one or more sheets of the filter material; and
stacking two or more of the sheets onto each other and/or winding the at least one of the one or more sheets around an inner cylinder to form the filter body,
the step of forming the one or more sheets comprises:
suspending cellulose fiber material having a dry first mass in water to form a cellulose fiber suspension comprising cellulose fibers in a singularized, swollen state, and
de-watering the cellulose fiber suspension, using gravity or gravity and vacuum, until the one or more sheets has (have) a wetted second mass, and the ratio of the dry first mass to the wetted second mass of the cellulose fiber network is 20-60%, and
the impregnating step is performed when the ratio of the dry first mass to the wetted second mass is 20-60%.

10. The method according to claim 6, wherein the impregnating comprises soaking only the first portion of the filter material in the separation aid or in a solution of the separation aid and water and/or spraying only the first portion of the filter material with the separation aid or with a solution of the separation aid and water and/or flowing the separation aid mixed with an oil over only the first portion of the filter material.

11. The method according to claim 6, further comprising drying the impregnated filter material to 90-100% of the dry mass of the network of cellulose fibers to the total mass of the network of cellulose fiber after the impregnating and prior to disposing the fiber body in the filter housing.

12. An oil purification filter produced according to the method of claim 6.

13. The oil purification filter according to claim 12, wherein the separation aid is bonded to the network of cellulose fibers in only the first portion of the filter body.

14. The oil purification filter according to claim 13, wherein the filter body comprises a plurality of sheets of the network of filter material arranged in layers to form a stack and/or at least one sheet of the network of filter material wound in layers around an inner cylinder.

15. An oil purification system comprising the oil purification filter according to claim 1, wherein said oil purification system is configured to be fluidly connected to a technical equipment which is using oil such that the oil is circulated through the oil purification filter for purification of the oil.

16. The oil purification system according to claim 15, comprising a filter housing in which said oil purification filter is removably provided, wherein:

an inlet of the filter is fluidly connected to an inlet of the filter housing, an outlet of the filter is fluidly connected to an outlet of the filter housing, and said oil purification system further comprises an inlet fluid connection fluidly connected to the inlet of the filter housing, and an outlet fluid connection fluidly connected to the outlet of the filter housing such that the contaminated oil is flowable into the inlet of the filter housing via the inlet fluid connection, through the filter housing and through the oil purification filter and further out from the filter housing through the outlet of the filter housing and further through the outlet fluid connection.

17. The oil purification system according to claim 16, further comprising at least one oil condition monitoring sensor for measuring a value indicative of a condition of an oil purified in said oil purification system.

18. The oil purification system according to claim 16, wherein:

the first portion of the filter material is disposed closer to the inlet than the second portion of the filter material, and the second portion of the filter material is disposed closer to the outlet than the first portion of the filter material.

19. The oil purification system according to claim 18, wherein the layers of the filter body are arranged in the filter housing such that the contaminated oil will flow predominantly along and parallel to the layers.

20. The oil purification filter according to claim 1, further comprising:

the filter housing having an inlet and an outlet, wherein:

only the first portion is impregnated with the separation aid, and the second portion is not impregnated with any separation aid, and the filter body is mounted in the filter housing such that the first portion of the filter body is closest to the inlet and the second portion of the filter body is closest to the outlet.

21. The oil purification filter according to claim 20, wherein:

the network of cellulose fibers is in the form of a stack or winding of one or more sheets that form layers of the sheet(s), a first lateral end of the layers is impregnated with the separation aid and is closest to the inlet, a second lateral end of the layers is not impregnated with the separation aid and is closest to the outlet, and the oil purification filter is configured to cause the contaminated oil to flow along and parallel to the layers between the inlet and the outlet.

* * * * *